(12) United States Patent
Kim et al.

(10) Patent No.: US 11,207,048 B2
(45) Date of Patent: Dec. 28, 2021

(54) X-RAY IMAGE CAPTURING APPARATUS AND METHOD OF CONTROLLING THE SAME

(71) Applicant: SAMSUNG ELECTRONICS CO., LTD., Suwon-si (KR)

(72) Inventors: Dong-wook Kim, Yongin-si (KR); Min-cheol Park, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 290 days.

(21) Appl. No.: 15/788,983

(22) Filed: Oct. 20, 2017

(65) Prior Publication Data
US 2018/0168535 A1 Jun. 21, 2018

(30) Foreign Application Priority Data
Dec. 21, 2016 (KR) .................. 10-2016-0175838

(51) Int. Cl.
*A61B 6/00* (2006.01)
*A61B 6/06* (2006.01)

(52) U.S. Cl.
CPC ............ *A61B 6/548* (2013.01); *A61B 6/4417* (2013.01); *A61B 6/4452* (2013.01); *A61B 6/4464* (2013.01); *A61B 6/461* (2013.01); *A61B 6/587* (2013.01); *A61B 6/06* (2013.01)

(58) Field of Classification Search
CPC ....... A61B 6/587; A61B 6/548; A61B 6/4417; A61B 6/4452; A61B 6/4464; A61B 6/461; A61B 6/06
See application file for complete search history.

(56) References Cited

U.S. PATENT DOCUMENTS

| | | | | | |
|---|---|---|---|---|---|
| 5,267,295 | A | * | 11/1993 | Strommer | H05G 1/64 378/108 |
| 5,623,528 | A | * | 4/1997 | Takeda | G01N 23/044 378/2 |
| 6,151,383 | A | * | 11/2000 | Xue | A61B 6/00 378/108 |
| 6,392,237 | B1 | * | 5/2002 | Agano | G01V 5/0041 250/370.11 |
| 6,405,072 | B1 | * | 6/2002 | Cosman | A61B 6/5247 600/426 |
| 6,447,163 | B1 | * | 9/2002 | Bani-Hashemi | A61B 6/08 378/205 |

(Continued)

FOREIGN PATENT DOCUMENTS

| | | |
|---|---|---|
| JP | 2013127672 A | 6/2013 |
| KR | 101427828 B1 | 8/2014 |
| KR | 1020160057939 A | 5/2016 |

*Primary Examiner* — David P Porta
*Assistant Examiner* — Djura Malevic
(74) *Attorney, Agent, or Firm* — Sughrue Mion, PLLC

(57) ABSTRACT

A method of controlling an X-ray image capturing apparatus, including acquiring, using a camera, a first image by photographing a detector configured to receive X-rays emitted from an X-ray emission surface, generating a second image by performing a correction on the first image, wherein the correction includes changing a first detector shape in the first image to match a second detector shape photographed in a direction perpendicular to the X-ray emission surface, and displaying the second image.

19 Claims, 11 Drawing Sheets

(56) References Cited

U.S. PATENT DOCUMENTS

| | | | | |
|---|---|---|---|---|
| 6,472,665 | B1* | 10/2002 | Ishisaka | G01T 1/2018 250/368 |
| 6,795,526 | B2* | 9/2004 | Kump | A61B 6/00 378/116 |
| 7,209,543 | B2* | 4/2007 | Strommer | A61B 6/502 378/108 |
| 7,885,439 | B2* | 2/2011 | Kato | A61B 5/489 382/128 |
| 8,203,132 | B2* | 6/2012 | Feke | A61B 5/0059 250/583 |
| 8,559,689 | B2* | 10/2013 | Mizuno | G06T 7/0014 382/128 |
| 8,633,445 | B2* | 1/2014 | Star-Lack | A61B 6/032 250/363.02 |
| 9,545,526 | B1* | 1/2017 | Partain | A61N 5/1067 |
| 9,547,896 | B2* | 1/2017 | Choi | G06T 7/0012 |
| 9,855,018 | B2* | 1/2018 | Hamano | A61B 6/563 |
| 9,974,504 | B2* | 5/2018 | Lee | A61B 6/465 |
| 10,285,656 | B2* | 5/2019 | Wang | A61B 6/4405 |
| 10,285,664 | B2* | 5/2019 | Song | A61B 6/4417 |
| 10,368,826 | B2* | 8/2019 | Tamura | A61B 6/4233 |
| 10,390,781 | B2* | 8/2019 | Park | A61B 6/502 |
| 10,481,111 | B2* | 11/2019 | Hench | G01N 23/083 |
| 10,660,599 | B2* | 5/2020 | Becker | A61B 6/547 |
| 10,849,589 | B2* | 12/2020 | Song | G01T 1/17 |
| 10,914,694 | B2* | 2/2021 | Ullom | G01T 1/36 |
| 10,930,028 | B2* | 2/2021 | Chen | A61B 6/545 |
| 2002/0012450 | A1* | 1/2002 | Tsujii | H04N 5/32 382/103 |
| 2003/0216631 | A1* | 11/2003 | Bloch | G06T 3/0081 600/407 |
| 2004/0005027 | A1* | 1/2004 | Nafstadius | A61N 5/1049 378/65 |
| 2004/0125921 | A1* | 7/2004 | Allouche | A61B 6/544 378/207 |
| 2005/0169425 | A1* | 8/2005 | Takasawa | A61B 6/547 378/97 |
| 2005/0265606 | A1* | 12/2005 | Nakamura | G06T 7/0012 382/218 |
| 2006/0269049 | A1* | 11/2006 | Yin | A61N 5/1048 378/207 |
| 2007/0223650 | A1* | 9/2007 | Francke | A61B 6/025 378/21 |
| 2008/0063249 | A1* | 3/2008 | Ohtsuka | A61B 6/4283 382/131 |
| 2008/0205588 | A1* | 8/2008 | Kim | A61B 6/4447 378/20 |
| 2008/0306379 | A1* | 12/2008 | Ikuma | A61B 5/065 600/424 |
| 2009/0086926 | A1* | 4/2009 | Wang | A61B 6/4405 378/206 |
| 2009/0097730 | A1* | 4/2009 | Kasai | A61B 6/00 382/132 |
| 2009/0122952 | A1* | 5/2009 | Nishide | A61B 6/032 378/4 |
| 2009/0135994 | A1* | 5/2009 | Yu | A61B 6/032 378/5 |
| 2010/0111395 | A1* | 5/2010 | Tamakoshi | A61B 6/469 382/132 |
| 2010/0145197 | A1* | 6/2010 | Stapf | A61B 5/416 600/445 |
| 2011/0013752 | A1* | 1/2011 | Takahashi | A61B 6/583 378/205 |
| 2011/0110497 | A1* | 5/2011 | Nishino | A61B 6/542 378/98.8 |
| 2011/0129058 | A1* | 6/2011 | Ulrici | A61B 6/14 378/4 |
| 2011/0254922 | A1* | 10/2011 | Schaerer | A61B 90/96 348/46 |
| 2012/0035462 | A1* | 2/2012 | Maurer, Jr. | A61B 5247 600/411 |
| 2012/0093280 | A1* | 4/2012 | Konno | A61B 6/032 378/7 |
| 2013/0057547 | A1* | 3/2013 | Hwang | G06T 17/00 345/420 |
| 2013/0070906 | A1* | 3/2013 | Suwa | A61B 6/4405 378/177 |
| 2013/0286174 | A1* | 10/2013 | Urakabe | A61B 1/00009 348/66 |
| 2014/0016752 | A1* | 1/2014 | Sugiyama | G01T 1/2002 378/62 |
| 2014/0016753 | A1* | 1/2014 | Sugiyama | G01T 1/2002 378/62 |
| 2014/0079185 | A1* | 3/2014 | Omi | H04N 5/23293 378/62 |
| 2014/0284485 | A1* | 9/2014 | Nagano | G01T 1/2006 250/366 |
| 2014/0348387 | A1* | 11/2014 | Choi | G06T 7/0012 382/103 |
| 2014/0355735 | A1* | 12/2014 | Choi | A61B 6/464 378/8 |
| 2015/0157289 | A1* | 6/2015 | Park | H04W 72/0406 600/407 |
| 2015/0164440 | A1* | 6/2015 | Rackow | A61B 5/7485 600/427 |
| 2015/0201892 | A1* | 7/2015 | Hummel | A61B 90/37 348/77 |
| 2015/0223767 | A1* | 8/2015 | Sehnert | A61B 6/4411 378/42 |
| 2015/0272520 | A1* | 10/2015 | Kobayashi | A61B 6/487 378/62 |
| 2015/0374314 | A1* | 12/2015 | Maack | A61B 6/588 378/62 |
| 2016/0114190 | A1* | 4/2016 | Brown | A61N 5/1075 378/205 |
| 2016/0154125 | A1* | 6/2016 | Kim | A61B 6/44 378/189 |
| 2016/0174918 | A1* | 6/2016 | Wang | A61B 6/588 378/63 |
| 2016/0331334 | A1* | 11/2016 | Imamura | A61B 6/06 |
| 2017/0027533 | A1* | 2/2017 | Sakaguchi | A61B 6/544 |
| 2017/0106885 | A1* | 4/2017 | Singh | G01B 11/22 |
| 2017/0281107 | A1* | 10/2017 | Park | A61B 6/542 |
| 2017/0281108 | A1* | 10/2017 | Choi | A61B 6/0414 |
| 2017/0360394 | A1* | 12/2017 | Deinlein | A61B 6/587 |
| 2018/0070911 | A1* | 3/2018 | Franklin | A61B 6/4429 |
| 2018/0092613 | A1* | 4/2018 | Ancar | A61B 6/08 |
| 2018/0153485 | A1* | 6/2018 | Rahmes | A61B 6/5241 |

* cited by examiner

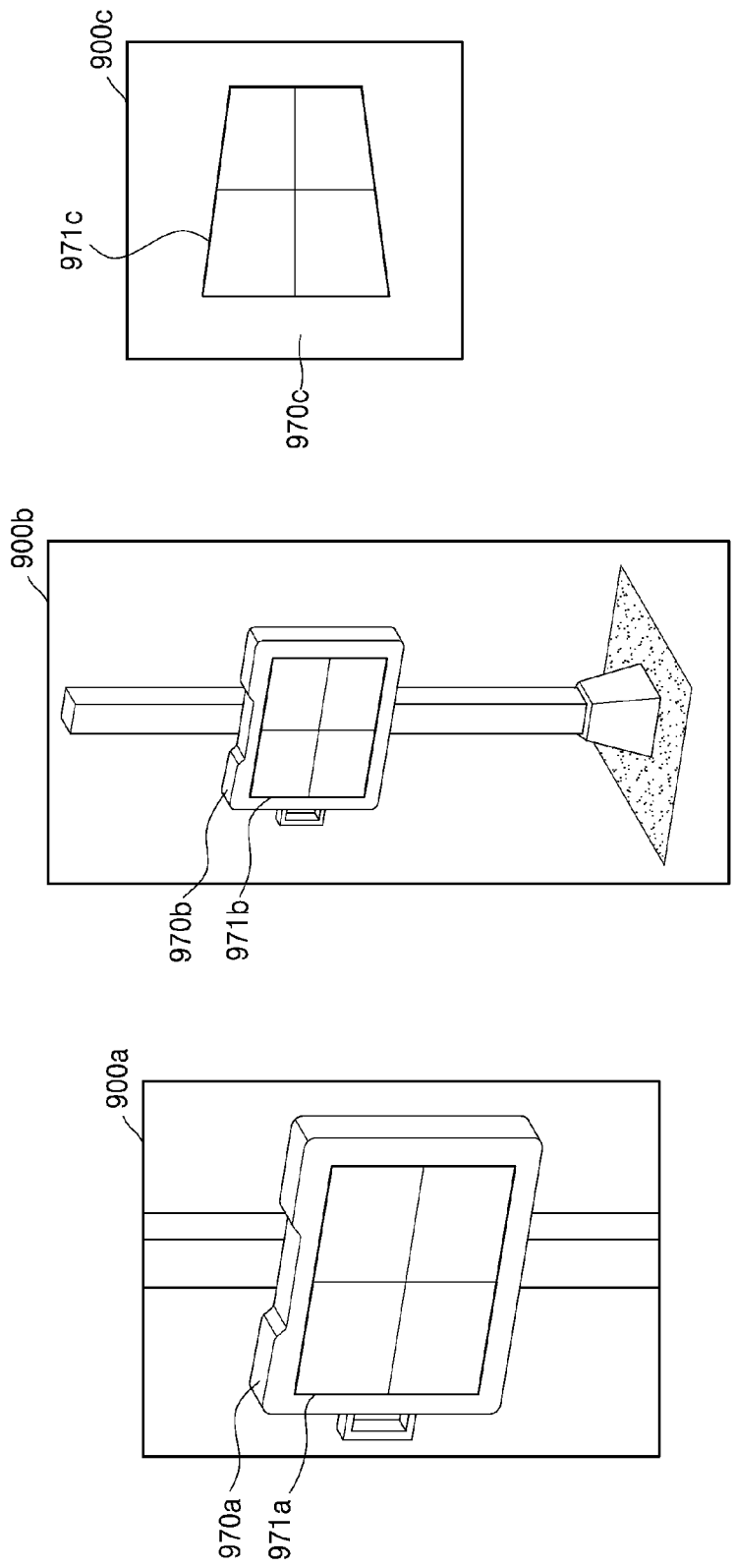

X-RAY IMAGE CAPTURING APPARATUS AND METHOD OF CONTROLLING THE SAME

CROSS-REFERENCE TO RELATED APPLICATION

This application claims benefit from Korean Patent Application No. 10-2016-0175838, filed on Dec. 21, 2016, in the Korean Intellectual Property Office, the disclosure of which is incorporated herein in its entirety by reference.

BACKGROUND

1. Field

The present disclosure relates to X-ray image capturing apparatuses and methods of controlling the same.

2. Description of Related Art

X-ray image capturing apparatuses have been developed and used as radiographic image capturing apparatuses for medical diagnosis. In an X-ray image capturing apparatus, when X-rays emitted from an X-ray source pass through an object, a scintillator converts X-rays that are differentially transmitted, according to a density of the object, into visible light, and the visible light is then converted into an electrical signal by a photodiode. The X-ray image capturing apparatus creates a digital image of the object through which the X-rays have passed, by using the electrical signal.

In general, to prevent a radiologic technologist from being exposed to radiation, an X-ray radiator of an X-ray image capturing apparatus is separated from a workstation for controlling the X-ray image capturing apparatus. Thus, the radiologic technologist adjusts the position of the X-ray radiator appropriately relative to a patient for X-ray imaging, and obtains an X-ray image by controlling the X-ray image capturing apparatus from a space, for example an imaging control room, where the workstation is located.

However, a desired X-ray image may not be acquired if the radiologic technologist fails to position the X-ray radiator correctly relative to a body part to be X-rayed, or if a patient moves during control of the X-ray image capturing apparatus from the space where the workstation is located.

Furthermore, even when a radiologic technologist adjusts a position of an X-ray radiator in a mobile X-ray image capturing apparatus, X-rays may be irradiated onto a wrong position due to a distance between the X-ray radiator and an input device.

In this case, X-ray imaging must be performed again, and thus a patient may be exposed to more radiation due to the additional X-ray imaging.

SUMMARY

Provided are X-ray image capturing apparatuses and methods of controlling the X-ray image capturing apparatuses, whereby the amount of patient exposure to radiation is minimized by preventing unnecessary X-ray imaging.

Provided are non-transitory computer-readable recording media having recorded thereon a program for executing, on a computer, a method of controlling an X-ray image capturing apparatus whereby the amount of patient exposure to radiation is minimized by preventing unnecessary X-ray imaging.

Additional aspects will be set forth in part in the description which follows and, in part, will be apparent from the description, or may be learned by practice of the presented exemplary embodiments.

According to an aspect of an exemplary embodiment, a method of controlling an X-ray image capturing apparatus includes acquiring, using a camera, a first image by photographing a detector configured to receive X-rays emitted from an X-ray emission surface, generating a second image by performing a correction on the first image, wherein the correction includes changing a first detector shape in the first image to match a second detector shape photographed in a direction perpendicular to the X-ray emission surface, and displaying the second image.

The generating of the second image may include correcting the first image based on a position of the X-ray emission surface, and a position of the camera.

The correcting of the first image may include correcting the first image based on a position of a center of the X-ray emission surface, and a position of a center of a lens of the camera.

The generating of the second image may include correcting the first image based on a distance between the X-ray emission surface and the detector.

The generating of the second image may include correcting the first image based on a predetermined reference indicator for determining at least one of a position of the detector and the first detector shape.

The displaying of the second image may include displaying the predetermined reference indicator together with the second image.

The method may further include determining, based on the predetermined reference indicator, whether an X-ray radiation device including the X-ray emission surface is arranged at a predetermined position.

The method may further include determining whether an X-ray radiation device including the X-ray emission surface is arranged at a predetermined position, based on whether the second detector shape corresponds to a reference shape, wherein the reference shape may include a shape of a reference detector included in a reference image captured in a direction perpendicular to a surface of the detector opposite the X-ray emission surface.

The method of may further include displaying, based on a result of the determining, the predetermined position.

The method may further include receiving, from a user, a control signal for controlling movement of the X-ray emission surface, moving the X-ray emission surface in response to the received control signal, generating a third image by performing a second correction on the first image, wherein the second correction may include changing the first detector shape to match a third detector shape photographed in a direction perpendicular to the moved X-ray emission surface, and displaying the generated third image.

According to another aspect of an exemplary embodiment, an X-ray image capturing apparatus includes a camera configured to acquire a first image by photographing a detector configured to receive X-rays emitted from an X-ray emission surface, at least one processor configured to generate a second image by performing a correction on the first image, wherein the correction may include changing a first detector shape in the first image to match a second detector shape photographed in a direction perpendicular to the X-ray emission surface, and a display configured to display the second image.

The at least one processor may be further configured to correct the first image based on a position of the X-ray emission surface, and a position of the camera.

The at least one processor may be further configured to correct the first image based on a position of a center of the X-ray emission surface, and a position of a center of a lens of the camera.

The at least one processor may be further configured to correct the first image based on a distance between the X-ray emission surface and the detector.

The at least one processor may be further configured to correct the first image based on a predetermined reference indicator for determining at least one of a position of the detector and the first detector shape.

The display may be further configured to display the predetermined reference indicator together with the second image.

The at least one processor may be further configured to determine, based on the predetermined reference indicator, whether an X-ray radiation device including the X-ray emission surface is arranged at a predetermined position.

The at least one processor may be further configured to determine whether an X-ray radiation device including the X-ray emission surface is arranged at a predetermined position, based on whether the second detector shape corresponds to a reference shape, and the reference shape may include a shape of a reference detector included in a reference image captured in a direction perpendicular to a surface of the detector opposite the X-ray emission surface.

The display may be further configured to display, based on a result of the determining, the predetermined position.

The X-ray image capturing apparatus may further include an input device configured to receive from a user a control signal for controlling movement of the X-ray emission surface, wherein the at least one processor may be further configured to control the X-ray emission surface to move in response to the received control signal and generate a third image by performing a second correction on the first image, wherein the second correction may include changing the first detector shape to match a third detector shape photographed in a direction perpendicular to the moved X-ray emission surface, and wherein the display may be further configured to display the generated third image.

BRIEF DESCRIPTION OF THE DRAWINGS

These and/or other aspects will become apparent and more readily appreciated from the following description of the embodiments, taken in conjunction with the accompanying drawings in which:

FIGS. 9A through 9C illustrate images captured and acquired by a camera according to an exemplary embodiment;

DETAILED DESCRIPTION

Figure 1:
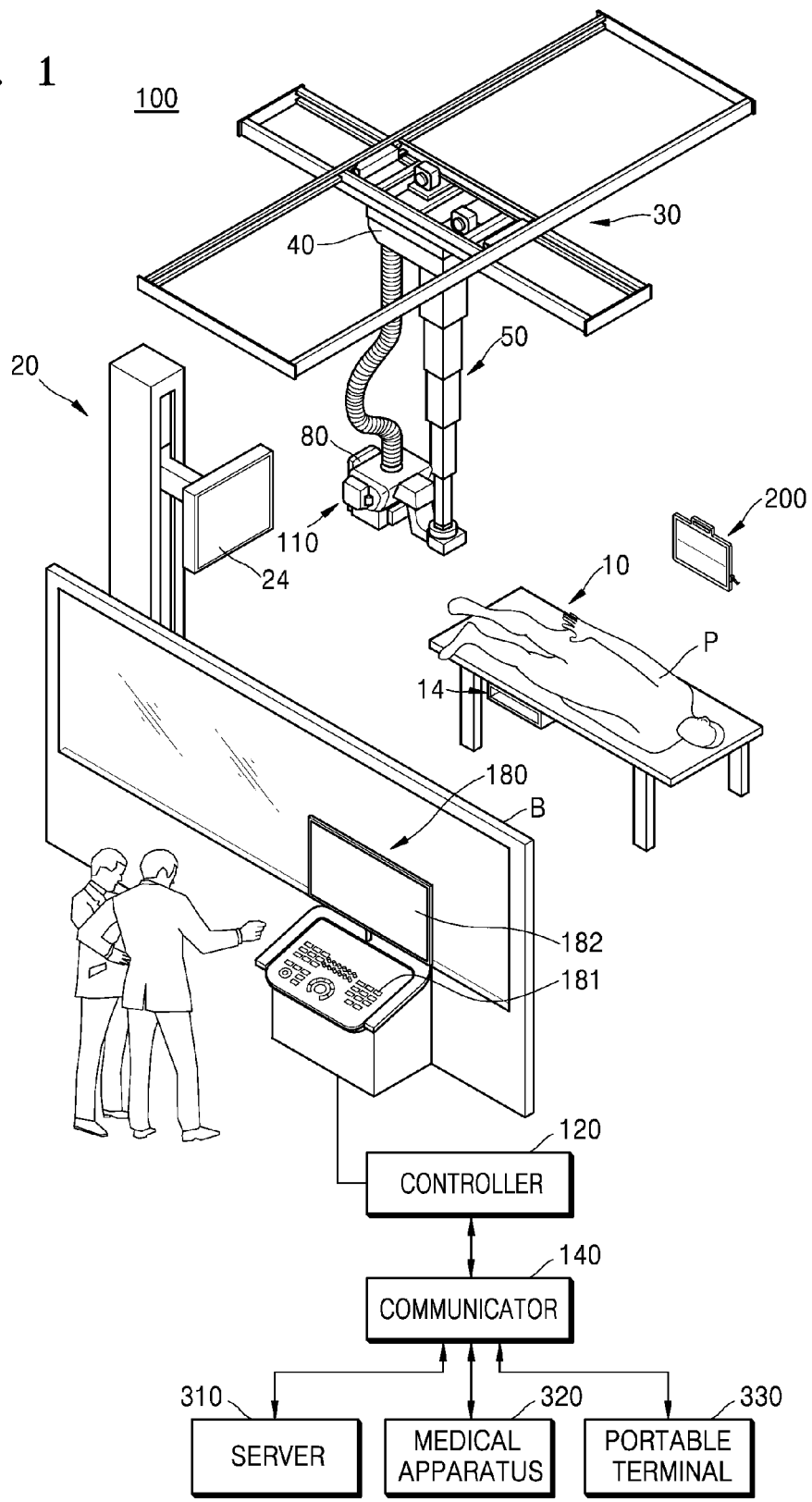
FIG. 1 is an external view and block diagram of a configuration of an X-ray apparatus according to an exemplary embodiment.

The present specification describes principles of the present disclosure and sets forth exemplary embodiments thereof to clarify the scope of the present disclosure and to allow those of ordinary skill in the art to implement the embodiments. The present exemplary embodiments may have different forms.

Like reference numerals refer to like elements throughout. The present specification does not describe all components in the exemplary embodiments, and common knowledge in the art or the same descriptions of the exemplary embodiments will be omitted below. The term "part" or "portion" may be implemented using hardware or software, and according to exemplary embodiments, one "part" or "portion" may be formed as a single unit or element or include a plurality of units or elements. Hereinafter, the principles and exemplary embodiments of the present disclosure will be described in detail with reference to the accompanying drawings.

In the present specification, an "image" may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and include a human, an animal, or a part of a human or animal. For example, the object may include a body part, such as an organ, or a phantom.

Hereinafter, exemplary embodiments will be described in detail with reference to the accompanying drawings.

<X-Ray Image Capturing Apparatus>

FIG. 1 is an external view and block diagram of a configuration of an X-ray apparatus 100 according to an exemplary embodiment. In FIG. 1, it is assumed that the X-ray apparatus 100 is a fixed X-ray apparatus.

Referring to FIG. 1, the X-ray apparatus 100 includes an X-ray radiation device for generating and emitting X-rays, an X-ray detector 200 for detecting X-rays that are emitted by the X-ray radiation device 110 and transmitted through an object P, and a workstation 180 for receiving a command from a user and providing information to the user. The X-ray apparatus 100 may further include a controller 120 for controlling the X-ray apparatus 100 according to the received command, and a communicator 140 for communicating with an external device.

All or some components of the controller 120 and the communicator 140 may be included in the workstation 180 or be separate from the workstation 180.

The X-ray radiation device 110 may include an X-ray source for generating X-rays and a collimator for adjusting a region irradiated with the X-rays generated by the X-ray source.

A guide rail 30 may be provided on a ceiling of an examination room in which the X-ray apparatus 100 is located, and the X-ray radiation device 110 may be coupled to a moving carriage 40 that is movable along the guide rail 30 such that the X-ray radiation device 110 may be moved to a position corresponding to the object P. The moving carriage 40 and the X-ray radiation device 110 may be connected to each other via a foldable post frame 50 such that a height of the X-ray radiation device 110 may be adjusted.

The workstation 180 may include an input device 181 for receiving a user command and a display 182 for displaying information.

The input device 181 may receive commands for controlling imaging protocols, imaging conditions, imaging timing, and locations of the X-ray radiation device 110. The input device 181 may include a keyboard, a mouse, a touch screen, a microphone, a voice recognizer, etc.

The display 182 may display a screen for guiding a user's input, an X-ray image, a screen for displaying a state of the X-ray apparatus 100, and the like.

The controller 120 may control imaging conditions and imaging timing of the X-ray radiation device 110 according to a command input by the user and may generate a medical image based on image data received from an X-ray detector 200. Furthermore, the controller 120 may control a position or orientation of the X-ray radiation device 110 or mount 14 and mount 24, each having the X-ray detector 200 mounted therein, according to imaging protocols and a position of the object P.

The controller 120 may include a memory configured to store programs for performing the operations of the X-ray apparatus 100 and a processor or a microprocessor configured to execute the stored programs. The controller 120 may include a single processor or a plurality of processors or microprocessors. When the controller 120 includes the plurality of processors, the plurality of processors may be integrated onto a single chip or be physically separated from one another.

The X-ray apparatus 100 may be connected to external devices such as an external server 310, a medical apparatus 320, and/or a portable terminal 330, for example a smart phone, a tablet PC, or a wearable device, in order to transmit or receive data via the communicator 140.

The communicator 140 may include at least one element capable of communicating with the external apparatus. For example, the communicator 140 may include at least one of a short-range communication module, a wired communication module, and a wireless communication module.

The communicator 140 may receive a control signal from an external device and transmit the received control signal to the controller 120 so that the controller 120 may control the X-ray apparatus 100 according to the received control signal.

In addition, by transmitting a control signal to an external device via the communicator 140, the controller 120 may control the external device according to the control signal. For example, the external device may process data of the external device according to the control signal received from the controller 120 via the communicator 140.

The communicator 140 may further include an internal communication module that enables communications between components of the X-ray apparatus 100. A program for controlling the X-ray apparatus 100 may be installed on the external device and may include instructions for performing some or all of the operations of the controller 120.

The program may be preinstalled on the portable terminal 330, or a user of the portable terminal 330 may download the program from a server providing an application for installation. The server that provides applications may include a recording medium where the program is stored.

Furthermore, the X-ray detector 200 may be implemented as a fixed X-ray detector that is fixedly mounted to a stand 20 or a table 10 or as a portable X-ray detector that may be detachably mounted in mount 14 or mount 24 or can be used at arbitrary positions. The portable X-ray detector may be implemented as a wired or wireless detector according to a data transmission technique and a power supply method.

The X-ray detector 200 may or may not be a component of the X-ray apparatus 100. If the X-ray detector 200 is not a component of the X-ray apparatus 100, the X-ray detector 200 may be registered by the user with the X-ray apparatus 100. Furthermore, in both cases, the X-ray detector 200 may be connected to the controller 120 via the communicator 140 to receive a control signal from or transmit image data to the controller 120.

A sub-user interface 80 that provides information to a user and receives a command from the user_may be provided on one side of the X-ray radiation device 110. The sub-user interface 80 may also perform some or all of the functions performed by the input device 181 and the display 182 of the workstation 180.

When all or some components of the controller 120 and the communicator 140 are separate from the workstation 180, they may be included in the sub-user interface 80 provided on the X-ray radiation device 110.

Although FIG. 1 shows a fixed X-ray apparatus connected to the ceiling of the examination room, examples of the X-ray apparatus 100 may include a C-arm type X-ray apparatus, a mobile X-ray apparatus, and other X-ray apparatuses having various structures that will be apparent to those of ordinary skill in the art.

Figure 2:
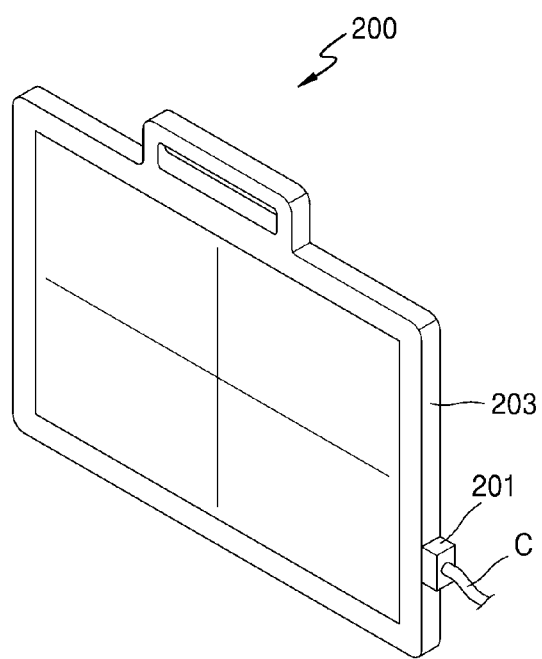
FIG. 2 is an external view of a portable X-ray detector according to an exemplary embodiment.

FIG. 2 is an external view of the X-ray detector 200.

As described above, the X-ray detector 200 used in the X-ray apparatus 100 may be implemented as a portable X-ray detector. The X-ray detector 200 may be equipped with a battery for supplying power to operate wirelessly, or as shown in FIG. 2, may operate in a manner that a charge port 201 is connected to a separate power supply via a cable C.

A case 203 maintains an external appearance of the X-ray detector 200 and has therein a plurality of detecting elements for detecting X-rays and converting the X-rays into image data, a memory for temporarily or permanently storing the image data, a communication module for receiving a control signal from the X-ray apparatus 100 or transmitting the image data to the X-ray apparatus 100, and a battery. Further, image correction information and intrinsic identification (ID) information of the X-ray detector 200 may be stored in the memory, and the stored ID information may be transmitted together with the image data during communication with the X-ray apparatus 100.

Figure 3:
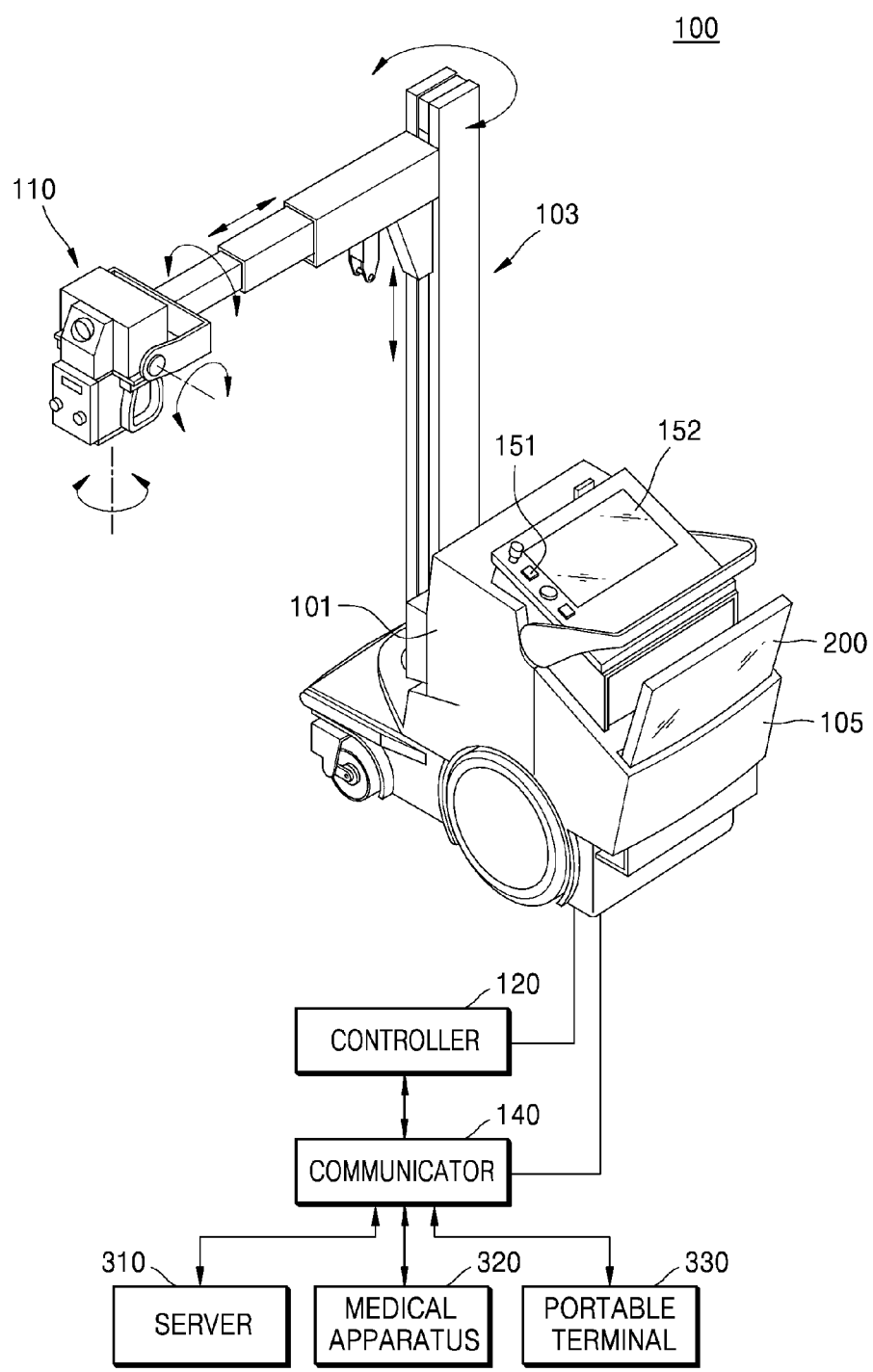
FIG. 3 is an external view and block diagram of an X-ray apparatus implemented as a mobile X-ray apparatus, according to an exemplary embodiment.

FIG. 3 is an external view and block diagram of an X-ray apparatus 100 implemented as a mobile X-ray apparatus, according to an exemplary embodiment.

Because components of the X-ray apparatus 100 of FIG. 3 perform the same functions as those of their counterparts shown in FIG. 1, detailed descriptions thereof are omitted below.

The X-ray apparatus 100 may be implemented as a mobile X-ray apparatus as well as a ceiling-mounted X-ray apparatus as described above. When the X-ray apparatus 100 is implemented as a mobile X-ray apparatus, a main body 101 connected to the X-ray radiation device 110 is freely movable, and an arm 103 connecting the X-ray radiation device 110 and the main body 101 to each other is rotatable and linearly movable. Thus, the X-ray radiation device 110 may be moved freely in a three-dimensional (3D) space.

A holder 105 may be formed on the main body 101 to accommodate the X-ray detector 200. A charging terminal may be disposed in the holder 105 to charge the X-ray detector 200. Thus, the holder 105 may be used to accommodate and to charge the X-ray detector 200.

The input device 151, the display 152, the controller 120, and the communicator 140 may be provided on the main body 101. Image data acquired by the X-ray detector 200 may be transmitted to the main body 101 for image processing, and then the resulting image may be displayed on the display 152 or transmitted to an external device via the communicator 140.

The controller 120 and the communicator 140 may be separate from the main body 101, or only some components of the controller 120 and the communicator 140 may be provided on the main body 101.

Figure 4:
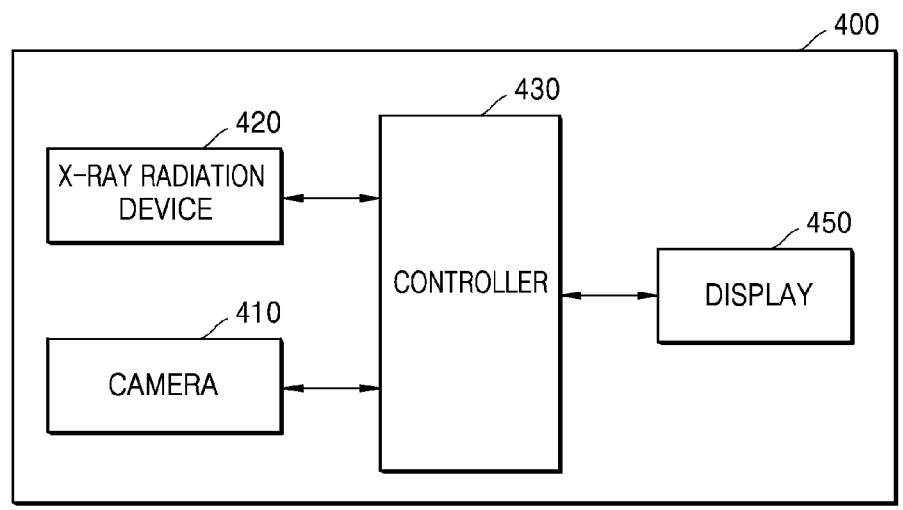
FIG. 4 is a block diagram of a configuration of an X-ray image capturing apparatus according to an exemplary embodiment.
Figure 5:
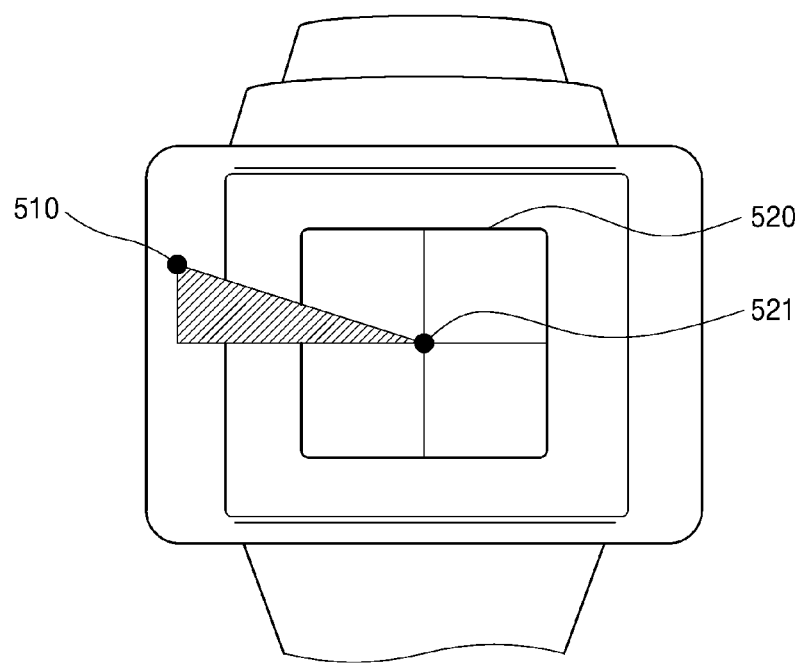
FIG. 5 illustrates an X-ray radiation device included in an X-ray image capturing apparatus according to an exemplary embodiment.

FIG. 4 is a block diagram of a configuration of an X-ray image capturing apparatus 400 according to an exemplary embodiment, and FIG. 5 illustrates an X-ray radiation device 500 included in an X-ray image capturing apparatus according to an exemplary embodiment.

Referring to FIG. 4, the X-ray image capturing apparatus 400 according to the present exemplary embodiment may include a camera 410, an X-ray radiation device 420, a controller 430, and a display 450. The camera 410 may be separated from the X-ray radiation device 420.

Referring to FIG. 5, a camera 510 may be positioned on one surface of the X-ray radiation device 500. The camera 510 may be spaced apart from an X-ray emission surface by a preset distance. For example, a center of a lens of the camera 510 may be spaced apart from a center 521 of the X-ray emission surface 520 by a preset distance. The camera 510 and the X-ray emission surface 520 may be arranged in the same plane.

Referring to FIG. 4, the camera 410 may acquire a first image by photographing the X-ray detector 200. According to an exemplary embodiment, the camera 410 may photograph the X-ray detector 200 that receives X-rays emitted from an X-ray emission surface in the X-ray radiation device 420. The camera 410 may acquire a first image including a photographed first detector. The first detector in the first image acquired by the camera 410 may have a distorted shape with one side longer than the other. Furthermore, the first detector in the first image may have a different shape than that of a second detector in a second image, which is photographed from an X-ray emission surface, due to a 3D position difference between the camera 410 and the X-ray emission surface.

According to an exemplary embodiment, the camera 410 may acquire consecutive first images in real-time. For example, the camera 410 may acquire a first image as a moving image in real-time.

The X-ray radiation device 420 may include the X-ray emission surface and a collimator. The X-ray emission surface refers to a surface of the X-ray radiation device 420 from which X-rays are emitted. The collimator may adjust X-rays emitted by the X-ray radiation device 420.

Referring to FIG. 5, the X-ray radiation device 500 may have the camera 510 and the X-ray emission surface 520 located on one side. The camera 510 may acquire a first image that is tilted at a preset angle with respect to the X-ray emission surface 520.

The controller 430 may control imaging timing and imaging conditions of the X-ray radiation device 420 according to a command input by the user and generate a medical image based on image data received from the X-ray detector 200 of FIG. 3. Furthermore, the controller 430 may control a position or orientation of the X-ray radiation device 420 or mount 14 and mount 24 of FIG. 1, each having the X-ray detector 200 mounted therein, according to imaging protocols and a position of the object P.

The controller 430 may include a memory configured to store programs for performing the above operations of the X-ray image capturing apparatus 400 as well as operations thereof that will be described below, and a processor configured to execute the stored programs. The controller 430 may include a single processor or a plurality of processors. When the controller 430 includes the plurality of processors, the plurality of processors may be integrated onto a single chip or be physically separated from one another.

Furthermore, the controller 430 may correct a first image acquired by the camera 410 such that a first detector in the first image may have the same shape as a preset shape. According to an exemplary embodiment, the controller 430 may correct the first image such that the first detector in the first image may have the same shape as a second detector photographed in a direction perpendicular to an X-ray emission surface. The controller 430 may also generate a second image by correcting the first image such that the first detector in the first image may have the same shape as the second detector photographed in a direction perpendicular to the X-ray emission surface.

According to an exemplary embodiment, the controller 430 may generate a second image after correcting a first image acquired by the camera 410 based on 3D positions of the X-ray emission surface and the camera 410. For example, the controller 430 may generate the second image after correcting the first image based on 3D positions of a center of the X-ray emission surface and a center of a camera lens. In detail, the controller 430 may generate the second image by correcting, based on 3D positions of centers of the X-ray emission surface and a camera lens, the first image such that the first detector in the first image may have the same shape as the second detector photographed in a direction perpendicular to the X-ray emission surface.

According to an exemplary embodiment, the controller 430 may correct a first image acquired by the camera 410 based on a difference between 3D positions of the X-ray emission surface and the X-ray detector 200 and generate a second image as a corrected version of the first image.

According to an exemplary embodiment, the controller 430 may correct a first image acquired by the camera 410 based on 3D positions of the X-ray emission surface and the camera 410 and a difference between 3D positions of the X-ray emission surface and the X-ray detector 200 and generate a second image as a corrected version of the first image.

According to an exemplary embodiment, the controller 430 may correct, based on a preset reference for determining a shape of a first detector in a first image acquired by the camera 410, the first image such that the first detector may have the same shape as a second detector photographed in a direction perpendicular to the X-ray emission surface, and generate a second image as a corrected version of the first image. For example, the controller 430 may correct a first image based on at least one of a vertex, an edge, and a center of the X-ray detector 200, a vertex, an edge, and a center of an X-ray detection surface positioned, to detect X-rays, opposite to the X-ray emission surface included in the X-ray radiation device 420, a vertex, an edge, and a center of a first detector in the first image, and a vertex, an edge, and a center of an X-ray detection surface included in the first detector, and generate a second image as a corrected version of the first image.

According to an exemplary embodiment, the controller 430 may correct, based on a preset reference for determining a position of the X-ray detector 200, a first image acquired by the camera 410 such that the first detector in the first image may have the same shape as a second detector photographed in a direction perpendicular to the X-ray emission surface, and generate a second image as a corrected version of the first image. For example, the controller 430 may correct a first image based on at least one of a vertex, an edge, and a center of the X-ray detector 200, a vertex, an edge, and a center of an X-ray detection surface positioned, to detect X-rays, opposite to the X-ray emission surface included in the X-ray radiation device 420, a vertex, an edge, and a center of a first detector in the first image, and a vertex, an edge, and a center of an X-ray detection surface included in the first detector, and generate a second image as a corrected version of the first image.

Image correction will be described in more detail below with reference to FIGS. 7A and 7B.

According to an exemplary embodiment, the controller 430 may control the display 450 to display in a second image a preset reference for determining at least one of a shape of a first detector in a first image acquired by the camera 410 and a position of the X-ray detector 200. For example, the controller 430 may control the display 450 to display, in the second image, at least one of a vertex, an edge, and a center of the X-ray detector 200, a vertex, an edge, and a center of an X-ray detection surface positioned, to detect X-rays, opposite to the X-ray emission surface included in the X-ray radiation device 420, a vertex, an edge, and a center of the first detector in the first image, and a vertex, an edge, and a center of an X-ray detection surface included in the first detector.

According to an exemplary embodiment, the controller 430 may determine whether the X-ray radiation device 420 is arranged at a preset position, based on a preset reference for determining at least one of a shape of a first detector in a first image acquired by the camera 410 and a position of the X-ray detector 200. For example, the controller 430 may determine whether the X-ray radiation device 420 is located at a preset position, based on at least one of a vertex, an edge, and a center of the X-ray detector 200, a vertex, an edge, and a center of an X-ray detection surface positioned, to detect X-rays, opposite to the X-ray emission surface included in the X-ray radiation device 420, a vertex, an edge, and a center of the first detector in the first image, and a vertex, an edge, and a center of an X-ray detection surface included in the first detector.

According to an exemplary embodiment, the controller 430 may determine whether the X-ray radiation device 420 is arranged at a preset position based on a shape of a first detector in a first image acquired by the camera 410. Furthermore, the controller 430 may determine whether the X-ray radiation device 420 is arranged at a preset position, based on a shape of the first image or a shape of a second detector photographed in a direction perpendicular to the X-ray emission surface. The controller 430 may also determine whether the X-ray radiation device 420 is arranged at a preset position, based on whether a shape of the second detector corresponds to a reference shape that is a shape of a detector in an image captured in a direction perpendicular to a surface of an X-ray detector opposite to the X-ray emission surface.

According to an exemplary embodiment, the controller 430 may control the display 450 to display a preset position where the X-ray radiation device 420 is to be arranged together with a second image, based on a result of the determining whether the X-ray radiation device 420 is arranged at the preset position.

According to an exemplary embodiment, the controller 430 may control the X-ray radiation device 420 including an X-ray emission surface to move in response to a control signal for controlling movement of the X-ray radiation device 420. The controller 430 may control the X-ray radiation device 420 to be tilted in response to a control signal for controlling tilting of the X-ray radiation device 420 at a preset angle.

According to an exemplary embodiment, the controller 430 may correct a first image acquired by the camera 410 according to movement of the X-ray radiation device 420 including the X-ray emission surface. In detail, the controller 430 may correct the first image according to tilting of the X-ray radiation device 420 including the X-ray emission surface. The controller 430 may also generate a second image by correcting the first image such that a first detector in the first image may have the same shape as a second detector photographed in a direction perpendicular to an X-ray emission surface.

According to an exemplary embodiment, the display 450 may display a second image that is generated by correcting a first image such that a first detector in the first image may have the same shape as a second detector photographed in a direction perpendicular to an X-ray emission surface. The display 450 may also display a preset position where the X-ray radiation device 420 is to be arranged, together with the second image. Furthermore, the display 450 may display a direction in which the X-ray radiation device 420 is to move to the preset position for arrangement, together with the second image. Furthermore, the display 450 may display, together with the second image, the preset position at which the X-ray radiation device 420 is to be arranged and the direction in which the X-ray radiation device 420 is to move to the preset position for arrangement.

<Method of Controlling an X-Ray Image Capturing Apparatus>

Figure 6:
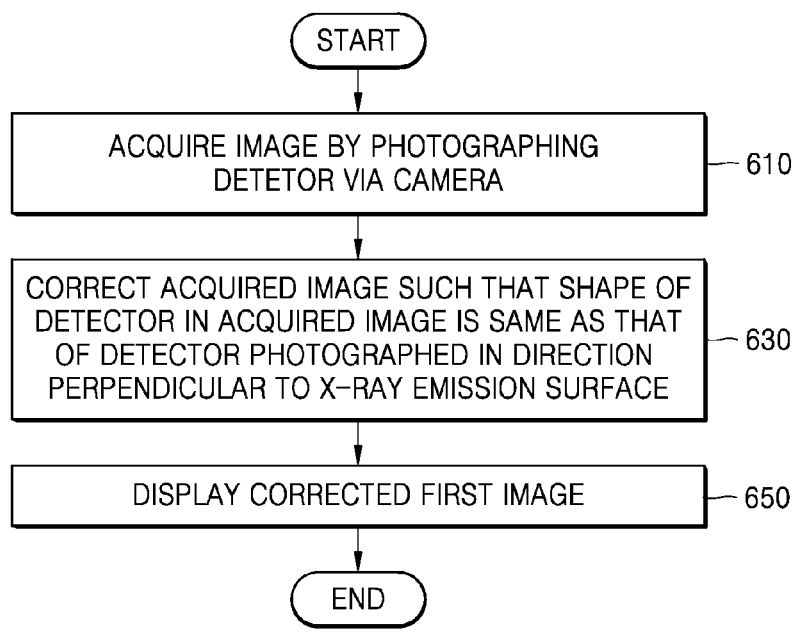
FIG. 6 is a flowchart of a method of controlling an X-ray image capturing apparatus, according to an exemplary embodiment.

FIG. 6 is a flowchart of a method of controlling the X-ray image capturing apparatus 400, according to an exemplary embodiment.

According to the present exemplary embodiment, the method of controlling the X-ray image capturing apparatus 400 may include acquiring a first image by photographing the X-ray detector 200 of FIG. 1 from the camera 410 at operation 610, correcting the first image such that a first detector in the first image may have the same shape as a second detector photographed in a direction perpendicular to an X-ray emission surface at operation 630, and generating and displaying a second image at operation 650.

Referring to operation 610, the X-ray image capturing apparatus 400 may acquire a first image by photographing, via the camera 410 included in the X-ray image capturing apparatus 400, the X-ray detector 200 for receiving X-rays emitted from an X-ray emission surface.

According to an exemplary embodiment, the X-ray image capturing apparatus 400 may acquire a first image by photographing the X-ray detector 200 via the camera 410 positioned on one surface of the X-ray radiation device 420. For example, the X-ray image capturing apparatus 400 may acquire the first image by photographing the X-ray detector 200 via the camera 410 that is spaced apart from the X-ray emission surface by a preset distance. The X-ray image capturing apparatus 400 may acquire the first image by photographing the X-ray detector 200 via the camera 410 that is spaced apart from a center of the X-ray emission surface by a preset distance. Furthermore, the X-ray image capturing apparatus 400 may acquire consecutive first images in real-time via the camera 410. The X-ray image capturing apparatus may also acquire the first image as a moving image in real-time via the camera 410.

Referring to operation 630, the X-ray image capturing apparatus 400 may correct the first image such that a first detector in the first image may have the same shape as a second detector photographed in a direction perpendicular to the X-ray emission surface and generate a second image as a corrected version of the first image.

According to an exemplary embodiment, because detectors are photographed to have different shapes due to a 3D position difference between the camera 410 and the X-ray emission surface, the X-ray image capturing apparatus 400 may correct the first image such that the detectors in images may have the same shape as each other and generate a second image as a corrected version of the first image.

According to an exemplary embodiment, the X-ray image capturing apparatus 400 may correct, based on at least one of 3D position differences between the X-ray emission surface and the camera 410 and between the X-ray emission surface and the X-ray detector 200, the first image such that a first detector may have the same shape as a second detector and generate a second image as a corrected version of the first image.

According to an exemplary embodiment, the X-ray image capturing apparatus 400 may correct the first image based on 3D positions of the X-ray emission surface and the camera 410 and generate the second image. Furthermore, the X-ray image capturing apparatus 400 may correct the first image based on positions of centers of the X-ray emission surface and the camera 410 and generate the second image. In addition, the X-ray image capturing apparatus 400 may correct the first image based on a distance between the X-ray emission surface and the X-ray detector 200 and generate the second image.

Image correction will be described in more detail below with reference to FIGS. 7A, 7B, 8, 9A through 9C, and 10A through 10C.

Referring to operation 650, the X-ray image capturing apparatus 400 may display the second image. A method of displaying the second image will be described in more detail below with reference to FIGS. 10A through 10C.

Figure 7A:
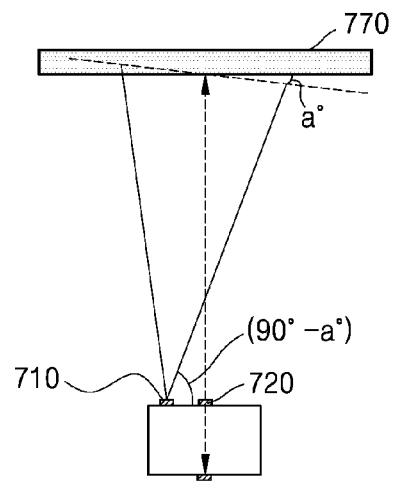
FIGS. 7A and 7B illustrate detectors being photographed according to three-dimensional (3D) positions of a camera and an X-ray emission surface according to an exemplary embodiment.
Figure 7B:
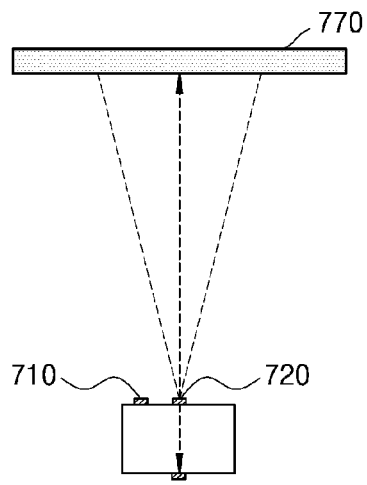

FIGS. 7A and 7B illustrate an X-ray detector 770 being photographed according to 3D positions of a camera 710 and an X-ray emission surface 720.

In detail, FIG. 7A shows the X-ray detector 770 photographed from the camera 710 according to an exemplary embodiment, and FIG. 7B shows the X-ray detector 770 photographed from the X-ray emission surface 720 according to an exemplary embodiment.

Referring to FIGS. 7A and 7B, the camera 710 acquires a first image by photographing the X-ray detector 770 to have a different shape than that of the X-ray detector 770 photographed from the X-ray emission surface 720 due to a 3D position difference between the camera 710 and the X-ray emission surface 720. For example, the camera 710 may acquire the first image by photographing the X-ray detector 770 to have a difference of a predetermined angle α° from the X-ray detector 770 photographed from the X-ray emission surface 720 due to a 3D position difference between the camera 710 and the X-ray emission surface 720. A first detector in the first image may have one side longer than the other unlike a second detector acquired from the X-ray emission surface 720, due to the 3D position difference between the camera 710 and the X-ray emission surface 720.

Figure 8:
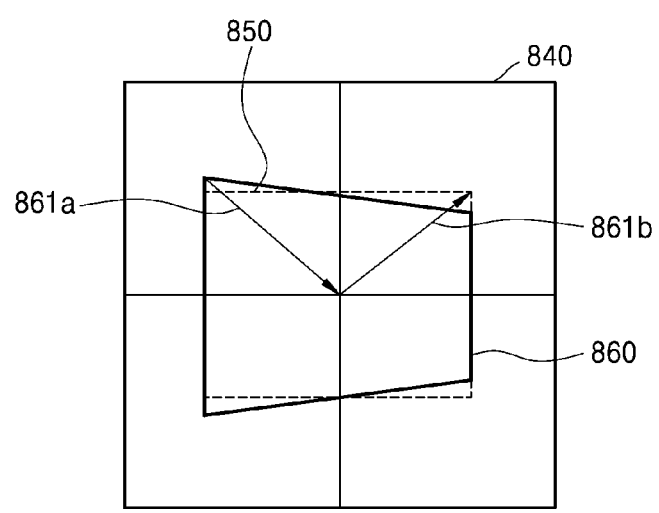
FIG. 8 illustrates an image captured and acquired by a camera and a method of correcting the image, according to an exemplary embodiment.

FIG. 8 illustrates an image captured and acquired by the camera 710 of FIGS. 7A and 7B and a corrected version of the image, according to an exemplary embodiment.

Referring to FIG. 8, a first detector 860 in a first image 840 acquired by photographing the X-ray detector 770 via the camera 710 may have a different shape than that of a second detector 850 photographed in a direction perpendicular to the X-ray emission surface 720. For example, the first detector 860 may have one side that is longer or shorter than that of the second detector 850 and the other side that is shorter or longer than that of the second detector 850. Furthermore, at least one of top/bottom and left/right of the first detector 860 may be asymmetrical.

According to an exemplary embodiment, when the camera 710 is positioned on the left side of the X-ray emission surface 720, the first detector 860 in the first image 840 acquired by photographing the X-ray detector 770 from the camera 710 may have a left side longer than a right side thereof. The first detector 860 may have the left and right sides that are respectively longer and shorter than those of the second detector 850.

According to an exemplary embodiment, the X-ray image capturing apparatus 400 may correct the first image 840 acquired by photographing the X-ray detector 770 via the camera 710, such that the first detector 860 in the first image 840 may have the same shape as the second detector 850 photographed in a direction perpendicular to the X-ray emission surface 720. For example, to make the shape of the first detector 860 equal to that of the second detector 850, the X-ray image capturing apparatus 400 may correct the first image 840 by extending the right side of the first detector 860 away from and shortening the left side thereof towards a center of the first image 840 or the first detector 860. The X-ray image capturing apparatus 400 may move a top left edge of the first detector 860 in a direction 861a of a center of the first detector 860, or the first image 840, while moving a top right edge of the first detector 860 away from the center of the first detector 860, or the first image 840, in a direction 861b of a top right edge of the second detector 850.

According to an exemplary embodiment, the X-ray image capturing apparatus 400 may correct, based on 3D positions of the camera 710 and the X-ray emission surface 720, the first image 840 acquired by photographing the X-ray detector 770 via the camera 710 such that the first detector 860 in the first image 840 may have the same shape as the second detector 850 photographed in a direction perpendicular to the X-ray emission surface 720. For example, the camera 710 may acquire the first image 840 by photographing the X-ray detector 770 to have a difference of a predetermined angle α° from the X-ray detector 770 photographed from the X-ray emission surface 720 due to a 3D position difference between the camera 710 and the X-ray emission surface 720. The X-ray image capturing apparatus 400 may calculate 3D positions of the camera 710 and the X-ray emission surface 720. The X-ray image capturing apparatus 400 may then calculate the predetermined angle α° based on the calculated 3D positions. The X-ray image capturing apparatus 400 may correct the first image 840 based on the calculated predetermined angle α° such that the first detector 860 may have the same shape as the second detector 850.

According to an exemplary embodiment, the X-ray image capturing apparatus 400 may correct the first image 840 based on 3D positions of a center of a lens of the camera 710 and a center of the X-ray emission surface 720, such that the first detector 860 in the first image 840 may have the same shape as the second detector 850 photographed in a direction perpendicular to the X-ray emission surface 720.

According to an exemplary embodiment, the X-ray image capturing apparatus 400 may correct the first image 840 based on 3D positions of the X-ray emission surface 720 and the X-ray detector 770, such that the first detector 860 in the first image 840 may have the same shape as the second detector 850 photographed in a direction perpendicular to the X-ray emission surface 720. In detail, the X-ray image capturing apparatus 400 may calculate the 3D positions of the X-ray emission surface 720 and the X-ray detector 770. The X-ray image capturing apparatus 400 may then calculate the predetermined angle α° based on the calculated 3D positions. The X-ray image capturing apparatus 400 may correct the first image 840 based on the calculated predetermined angle α° such that the first detector 860 may have the same shape as the second detector 850.

According to an exemplary embodiment, the X-ray image capturing apparatus 400 may correct, based on 3D positions of the camera 710, the X-ray emission surface 720, and the X-ray detector 770, the first image 840 acquired by photographing the X-ray detector 770 via the camera 710 such that the first detector 860 in the first image 840 may have the same shape as the second detector 850 photographed in a direction perpendicular to the X-ray emission surface 720. For example, the camera 710 may acquire the first image 840 by photographing the X-ray detector 770 to have a difference of the predetermined angle a° from the X-ray detector 770 photographed from the X-ray emission surface 720 due to 3D position differences among the camera 710, the X-ray emission surface 720, and the X-ray detector 770. As a 3D position difference between the camera 710 and the X-ray emission surface 720 increases, a 3D position difference between the X-ray emission surface 720 and the X-ray detector 770 decreases, and a 3D position difference between the camera 710 and the X-ray detector 770 decreases, the camera 710 may acquire an image having a larger predetermined angle a°. Furthermore, the X-ray image capturing apparatus 400 may correct the first image 840 to negate the predetermined angle a° based on 3D positions of the camera 710, the X-ray emission surface 720, and the X-ray detector 770. The X-ray image capturing apparatus 400 may correct the first image 840 to negate the difference of the predetermined angle a° by moving an edge of the first detector 860 in the direction 861a of the center of the first image 840, or the first detector 860, and another edge of the first detector 860 away from the center of the first image 840, or the first detector 860, in the direction 861b of the edge of the second detector 850.

Figure 10C:
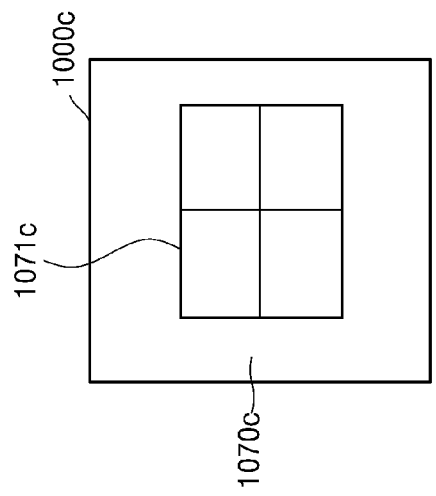
FIGS. 10A through 10C illustrate corrected images according to an exemplary embodiment.
Figure 10B:
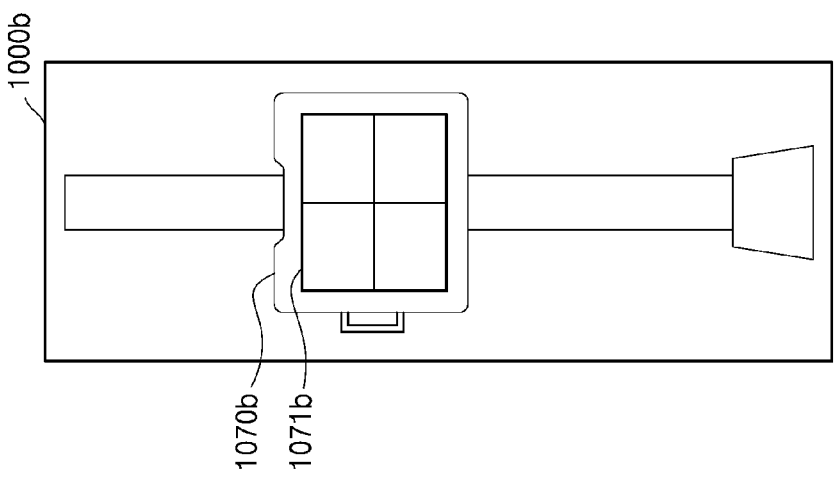
Figure 10A:
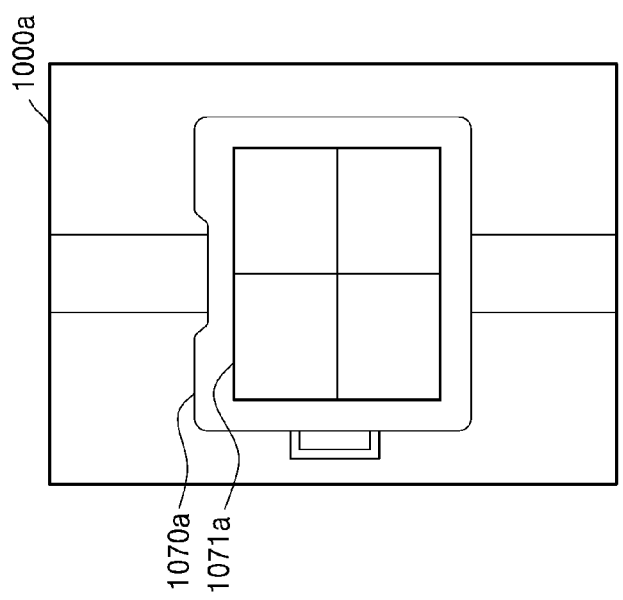

FIGS. 9A through 9C illustrate images captured and acquired by the camera 710 according to an exemplary embodiment, and FIGS. 10A through 10C illustrate corrected versions of the acquired images according to an exemplary embodiment.

Referring to FIGS. 9A through 9C and 10A through 10C, first detectors 970a, 970b, and 970c respectively in first images 900a, 900b, and 900c acquired by the camera 710 have different shapes than those of second detectors 1070a, 1070b, and 1070c photographed in a direction perpendicular to the X-ray emission surface 720, due to a 3D position difference between the camera 710 and the X-ray emission surface 720.

According to an exemplary embodiment, the X-ray image capturing apparatus 400 may acquire first images 900a, 900b, and 900c by photographing the X-ray detector 770 to have a difference of a predetermined angle a° from the X-ray detector 770 photographed from the X-ray emission surface 720 due to the 3D position difference between the camera 710 and the X-ray emission surface 720. The first detectors 970a, 970b, and 970c respectively in the first images 900a, 900b, and 900c may each have one side longer than the other compared to the second detectors 1070a, 1070b, and 1070c photographed in a direction perpendicular to the X-ray emission surface 720, due to the 3D position difference between the camera 710 and the X-ray emission surface 720.

According to an exemplary embodiment, the X-ray image capturing apparatus 400 may correct the first images 900a, 900b, and 900c based on a preset reference for determining a position of the X-ray detector 770, such that the first detectors 970a, 970b, and 970c respectively in the first images 900a, 900b, and 900c may have the same shapes as the second detectors 1070a, 1070b, and 1070c photographed in a direction perpendicular to the X-ray emission surface 720, and generate second images 1000a, 1000b, and 1000c as corrected versions of the first images 900a, 900b, and 900c. For example, the X-ray image capturing apparatus 400 may determine at least one 3D positions of the camera 710, the X-ray emission surface 720, and the X-ray detector 770 based on at least one of a vertex, an edge, and a center of the X-ray detector 770, a vertex, an edge, and a center of an X-ray detection surface positioned, to detect X-rays, opposite to the X-ray emission surface 720 included in the X-ray radiation device 420, a vertex, an edge, and a center of the first detector 970a, 970b, or 970c in the first image 900a, 900b, or 900c, and a vertex, an edge, and a center of an X-ray detection surface included in the first detector 970a, 970b, or 970c. The X-ray image capturing apparatus 400 may correct, based on the determined 3D positions of the camera 710, the X-ray emission surface 720, and the X-ray detector 770, the first images 900a, 900b, and 900c such that the first detectors 970a, 970b, and 970c may have the same shapes as the second detectors 1070a, 1070b, and 1070c, respectively, and generate the second images 1000a, 1000b, and 1000c. The X-ray image capturing apparatus 400 may calculate a 3D position of at least one of a vertex, an edge, and a center of the X-ray detector 770 and a vertex, an edge, and a center of an X-ray detection surface positioned, to detect X-rays, opposite to the X-ray emission surface 720 included in the X-ray radiation device 420, and a 3D position of at least one of the camera 710 and the X-ray emission surface 720. The X-ray image capturing apparatus 400 may then calculate a predetermined angle a° based on the calculated 3D positions. The X-ray image capturing apparatus 400 may correct, based on the calculated predetermined angle a°, the first images 900a, 900b, and 900c such that the first detectors 970a, 970b, and 970c may respectively have the same shapes as the second detectors 1070a, 1070b, and 1070c, and generate the second images 1000a, 1000b, and 1000c.

According to an exemplary embodiment, the X-ray image capturing apparatus 400 may correct, based on a preset reference for determining shapes of the first detectors 970a, 970b, and 970c respectively in the first images 900a, 900b, and 900c acquired by the camera 710, the first images 900a, 900b, and 900c such that the first detectors 970a, 970b, and 970c may have the same shapes as the second detectors 1070a, 1070b, and 1070c photographed in a direction perpendicular to the X-ray emission surface 720, and generate the second images 1000a, 1000b, and 1000c. For example, the controller 430 may correct the first images 900a, 900b, and 900c based on at least one of a vertex, an edge, and a center of the X-ray detector 770, a vertex, an edge, and a center of an X-ray detection surface positioned, to detect X-rays, opposite to the X-ray emission surface 720 included in the X-ray radiation device 420, a vertex, an edge, and a center of the first detector 970a, 970b, or 970c in the first image 900a, 900b, or 900c, and a vertex, an edge, and a center of an X-ray detection surface included in the first detector 970a, 970b, or 970c, and generate the second images 1000a, 1000b, and 1000c. As another example, the X-ray image capturing apparatus 400 may calculate a predetermined angle a° based on edges 971a, 971b, and 971c of X-ray detection surfaces respectively included in the first detectors 970a, 970b, and 970c. The X-ray image capturing apparatus 400 may correct, based on the calculated predetermined angle a°, the first images 900a, 900b, and 900c such that the first detectors 970a, 970b, and 970c may respectively have the same shapes as the second detectors 1070a, 1070b, and 1070c, and generate the second images 1000a, 1000b, and 1000c.

Referring to FIGS. 9A and 10A, the X-ray detector 770 may be implemented as a stand-type detector. The X-ray image capturing apparatus 400 may acquire the first image 900a by photographing the X-ray detector 770 to have a difference of a predetermined angle a° from the X-ray detector 770 photographed from the X-ray emission surface 720 due to a 3D position difference between the camera 710 and the X-ray emission surface 720. The first detector 970a in the first image 900a may have a right side longer than a left side thereof. The X-ray image capturing apparatus 400 may also calculate the predetermined angle a° based on 3D positions of at least two of the camera 710, the X-ray emission surface 720, and the X-ray detector 770. For example, the X-ray image capturing apparatus 400 may calculate the predetermined angle a° based on the edge 971a of the first detector 970a. The X-ray image capturing apparatus 400 may correct the first image 900a based on the calculated predetermined angle a° such that the first detector 970a may have the same shape as the second detector 1070a and generate the second image 1000a.

FIG. 9B shows the first image 900b acquired by the camera 710 that is spaced far apart from the X-ray detector 770, and FIG. 10B shows a corrected version 1000b of the first image 900b.

Referring to FIGS. 9B and 10B, a difference between lengths of right and left sides of the first detector 970b in the first image 900b acquired by the camera 710 is less than a difference between lengths of right and left sides of the first detector 970a shown in FIG. 9A. As a distance between the camera 710 and the X-ray detector 770 increases, a difference of a predetermined angle a° between the first detector 970b and the second detector 1070b photographed in a direction perpendicular to the X-ray emission surface 720 decreases. The X-ray image capturing apparatus 400 may also calculate the predetermined angle a° based on 3D positions of at least two of the camera 710, the X-ray emission surface 720, and the X-ray detector 770. For example, the X-ray image capturing apparatus 400 may calculate the predetermined angle a° based on a preset reference. The X-ray image capturing apparatus 400 may calculate the predetermined angle a° based on an edge 971b of an X-ray detection surface included in the first detector 970b. The X-ray image capturing apparatus 400 may correct the first image 900b based on the calculated predetermined angle a° such that the first detector 970b may have the same shape as the second detector 1070b, thereby generating the second image 1000b.

Referring to FIGS. 9C and 10C, the X-ray image capturing apparatus 400 may acquire the first image 900c by photographing the X-ray detector 770 to have a difference of a predetermined angle a° from the X-ray detector 770 photographed from the X-ray emission surface 720 due to a 3D position difference between the camera 710 and the X-ray emission surface 720. The first detector 970c in the first image 900c may have a left side longer than a right side thereof. The X-ray image capturing apparatus 400 may calculate the predetermined angle a° based on a preset reference. The X-ray image capturing apparatus 400 may calculate the predetermined angle a° based on the edge 971c of an X-ray detection surface included in the first detector 970c. The X-ray image capturing apparatus 400 may correct the first image 900c based on the calculated predetermined angle a° such that the first detector 970c may have the same shape as the second detector 1070c, thereby generating the second image 1000c.

Referring to FIGS. 10A through 10C, the X-ray image capturing apparatus 400 may respectively display preset references in the second images 1000a, 1000b, and 1000c. For example, the X-ray image capturing apparatus 400 may respectively display, in the second images 1000a, 1000b, and 1000c, edges 1071a, 1071b, and 1071c of X-ray detection surfaces respectively included in the second detector 1070a, 1070b, and 1070c.

Figure 11:
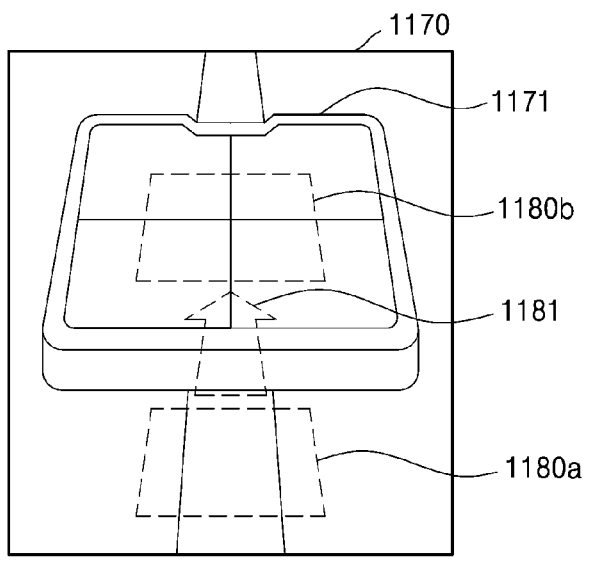
FIG. 11 illustrates a method of displaying a position of an X-ray radiation device, according to an exemplary embodiment.

FIG. 11 illustrates a method of displaying a position of the X-ray radiation device 420, according to an exemplary embodiment.

Referring to FIG. 11, the X-ray image capturing apparatus 400 may determine whether the X-ray radiation device 420 is arranged at a preset position.

According to an exemplary embodiment, the X-ray image capturing apparatus 400 may determine whether the X-ray radiation device 420 is arranged at a preset position, based on a preset reference. For example, the X-ray image capturing apparatus 400 may determine whether the X-ray radiation device 420 is arranged at a preset position, based on an edge of an X-ray detection surface included in a detector.

According to an exemplary embodiment, the X-ray image capturing apparatus 400 may determine whether the X-ray radiation device 420 is arranged at a preset position based on a shape of a second detector. For example, the X-ray image capturing apparatus 400 may determine whether the X-ray radiation device 420 is arranged at a preset position, based on whether a shape of the second detector corresponds to a reference shape that is a shape of a detector in a reference image captured in a direction perpendicular to a surface of an X-ray detector opposite to the X-ray emission surface.

According to an exemplary embodiment, the X-ray image capturing apparatus 400 may display a preset position where the X-ray radiation device 420 is to be arranged together with a second image, based on a result of the determining whether the X-ray radiation device 420 is arranged at the preset position. Referring to FIG. 11, for example, the X-ray image capturing apparatus 400 may display a preset position 1180b where an X-ray radiation device 1180a is to be arranged, together with a second image 1170.

According to an exemplary embodiment, the X-ray image capturing apparatus 400 may display a direction in which the X-ray radiation device 420 is to move to a preset position for arrangement, together with a second image. For example, the X-ray image capturing apparatus 400 may display a direction 1181 in which the X-ray radiation device 1180*a* is to move for arrangement, together with the second image 1170.

According to an exemplary embodiment, the X-ray image capturing apparatus 400 may display, together with a second image, a preset position at which the X-ray radiation device 420 is to be arranged and a direction in which the X-ray radiation device 420 is to move to the preset position for arrangement. For example, the X-ray image capturing apparatus 400 may display, together with the second image 1170, the preset position 1180*b* at which the X-ray radiation device 1180*a* is to be arranged and the direction 1181 in which the X-ray radiation device 1180*a* is to move to the preset position 1180*b* for arrangement.

Figure 12:
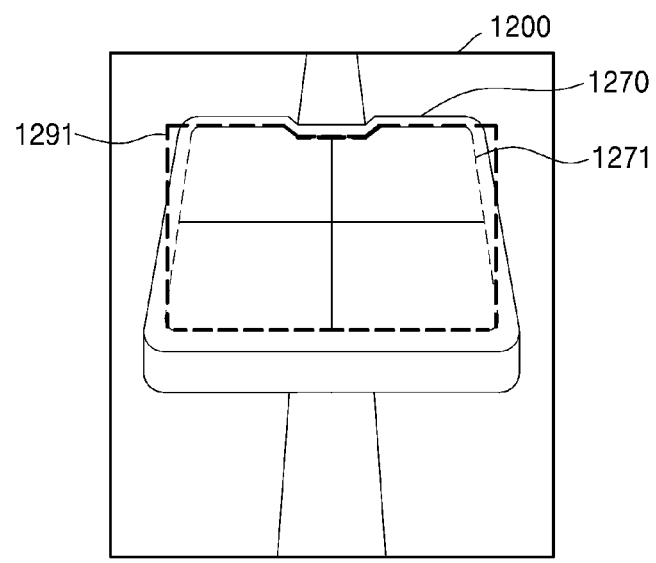
FIG. 12 illustrates a method of determining whether an X-ray radiation device is arranged at a preset position, according to an exemplary embodiment.

FIG. 12 illustrates a method of determining whether the X-ray radiation device 420 is arranged at a preset position, according to an exemplary embodiment.

Referring to FIG. 12, the X-ray image capturing apparatus 400 may determine whether the X-ray radiation device 420 is arranged at a preset position based on whether a shape of a second detector corresponds to a reference shape that is a shape of a detector in a reference image captured in a direction perpendicular to a surface of an X-ray detector opposite to the X-ray emission surface. For example, the X-ray image capturing apparatus 400 may determine whether the X-ray radiation device 420 is arranged at a preset position based on whether a shape 1271 of a second detector 1270 corresponds to a reference shape 1291 of a detector.

According to an exemplary embodiment, after comparing a shape of a second detector with a reference shape of a detector, the X-ray image capturing apparatus 400 may display a direction in which the X-ray radiation device 420 moves for arrangement at a preset position.

According to an exemplary embodiment, by comparing a shape of a second detector with a reference shape of a detector, the X-ray image capturing apparatus 400 may control the X-ray radiation device 420 such that the shape of the second detector is the same as the reference shape of the detector. For example, the X-ray image capturing apparatus 400 may control the X-ray radiation device 420 to move. The X-ray image capturing apparatus 400 may also tilt the X-ray radiation device 420 at a preset angle. The X-ray image capturing apparatus 400 may receive a signal for controlling the X-ray radiation device 420 from a user and control the X-ray radiation device 420 in response to the received signal.

According to an exemplary embodiment, when the X-ray radiation device 420 is arranged at a preset position, the X-ray image capturing apparatus 400 may display an alarm. For example, the X-ray image capturing apparatus 400 may display a notification indicating that the X-ray radiation device 420 is arranged at the preset position by using at least one of a color, a border, a letter, and a shape on a screen.

Figure 13:
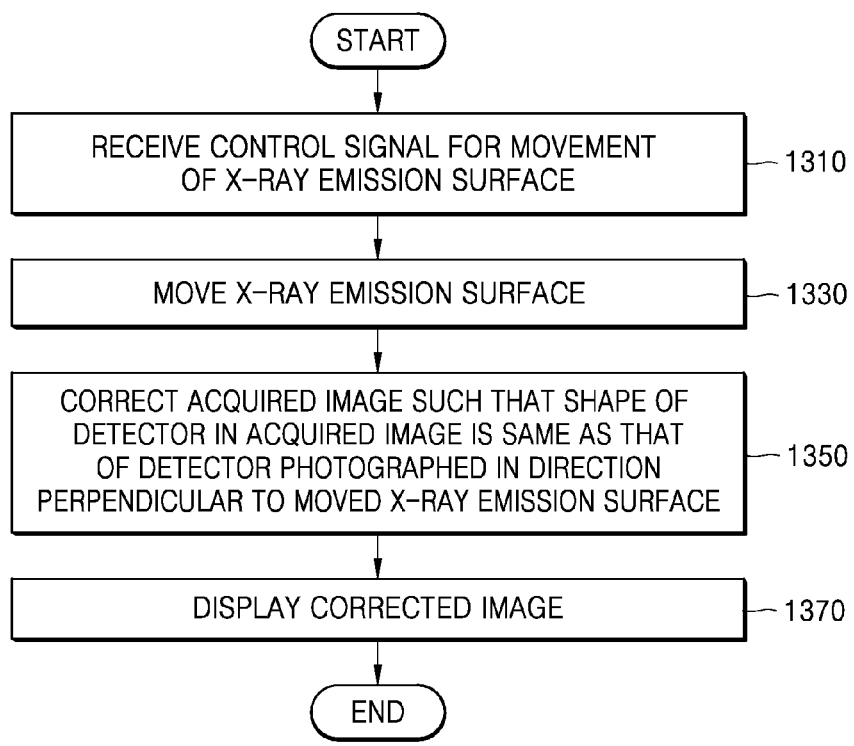
FIG. 13 is a flowchart of a method of controlling an X-ray image capturing apparatus, according to an exemplary embodiment.

FIG. 13 is a flowchart of a method of controlling the X-ray image capturing apparatus 400, according to an exemplary embodiment.

Referring to FIG. 13, the method of controlling the X-ray image capturing apparatus 400 may include receiving a control signal for controlling movement of an X-ray emission surface from a user at operation 1310, moving the X-ray emission surface in response to the received control signal at operation 1330, correcting a first image such that a first detector may have the same shape as a third detector photographed in a direction perpendicular to the moved X-ray emission surface and generating a third image at operation 1350, and displaying the third image at operation 1370.

Referring to operation 1310, the X-ray image capturing apparatus 400 may receive a control signal for controlling movement of an X-ray emission surface from a user.

According to an exemplary embodiment, the X-ray image capturing apparatus 400 may receive, via the input device 181 of FIG. 1 included in the workstation 180 of FIG. 1, a control signal for controlling movement of an X-ray emission surface from the user. For example, the X-ray image capturing apparatus 400 may receive a control signal for controlling movement of the X-ray radiation device 420 including an X-ray emission surface from the user. The X-ray image capturing apparatus 400 may receive, from the user, a control signal for tilting the X-ray radiation device 420 including the X-ray emission surface at a preset angle.

Referring to operation 1330, the X-ray image capturing apparatus 400 may control the X-ray emission surface to move in response to the received control signal for controlling movement of the X-ray emission surface. For example, the X-ray image capturing apparatus 400 may control the X-ray radiation device 420 to move in response to a control signal that is received from the user for controlling movement of the X-ray radiation device 420 including the X-ray emission surface. The X-ray image capturing apparatus 400 may control the X-ray radiation device 420 to be tilted at a preset angle in response to a control signal that is received from the user for titling the X-ray radiation device 420 including the X-ray emission surface at the preset angle.

Referring to operation 1350, the X-ray image capturing apparatus 400 may correct a first image such that a first detector in the first image may have the same shape as a third detector photographed in a direction perpendicular to the moved X-ray emission surface and generate a third image. For example, the X-ray image capturing apparatus 400 may correct a first image such that a first detector may have the same shape as a third detector photographed in a direction perpendicular to an X-ray emission surface included in the moved X-ray radiation device and generate a third image. Furthermore, the X-ray image capturing apparatus 400 may correct a first image such that a first detector may have the same shape as a third detector photographed in a direction perpendicular to an X-ray emission surface included in the X-ray radiation device tilted at a preset angle and generate a third image.

Referring to operation 1370, the X-ray image capturing apparatus 400 may display the third image. For example, the X-ray image capturing apparatus 400 may display a third image generated by correcting the first image such that a first detector in the first image may have the same shape as a third detector photographed in a direction perpendicular to the moved X-ray emission surface. Furthermore, the X-ray image capturing apparatus 400 may display the third image in such a manner that a shape of the first detector is the same as that of the third detector photographed in a direction perpendicular to the X-ray emission surface tilted at a preset angle. Furthermore, the X-ray image capturing apparatus 400 may correct the first image acquired via the camera 410 in real-time to thereby generate a third image and display the generated third image. The X-ray image capturing apparatus 400 may display a third image generated by correcting the acquired first image in response to movement of the X-ray radiation device 420 in real-time.

A method of controlling an X-ray image capturing apparatus according to an exemplary embodiment allows the user to accurately control an X-ray radiation device and capture an X-ray image, from a workstation that is physically separated from the X-ray radiation device. Furthermore, the method allows accurate X-ray imaging and thus eliminates the need for the user to perform unnecessary X-ray imaging, thereby reducing the amount of patient exposure to radiation.

<Recording Media>

Exemplary embodiments may be implemented through non-transitory computer-readable recording media having recorded thereon computer-executable instructions and data. The instructions may be stored in the form of program codes, and when executed by a processor, generate a predetermined program module to perform a specific operation. Furthermore, when being executed by the processor, the instructions may perform specific operations according to the exemplary embodiments.

What is claimed is:

1. A method of controlling an X-ray image capturing apparatus, the method comprising:
   acquiring, using a camera, a first image by photographing a detector configured to receive X-rays emitted from an X-ray emission surface;
   generating a second image by image processing the first image, wherein the image processing comprises performing a correction on the first image, wherein the correction comprises changing a first detector shape in the first image to match a second detector shape photographed in a direction perpendicular to the X-ray emission surface;
   identifying that the second detector shape corresponds to a shape of a reference detector included in a reference image captured in a direction perpendicular to a surface of the detector opposite the X-ray emission surface; and
   displaying the second image with the shape of the reference detector,
   wherein the generating of the second image comprises correcting the first image based on a position of the X-ray emission surface, and a position of the camera.

2. The method of claim 1, wherein the correcting of the first image comprises correcting the first image based on a position of a center of the X-ray emission surface, and a position of a center of a lens of the camera.

3. The method of claim 1, wherein the generating of the second image comprises correcting the first image based on a distance between the X-ray emission surface and the detector.

4. The method of claim 1, wherein the generating of the second image comprises correcting the first image based on a predetermined reference indicator for determining at least one of a position of the detector and the first detector shape.

5. The method of claim 4, wherein the displaying of the second image comprises displaying the predetermined reference indicator together with the second image.

6. The method of claim 4, further comprising determining, based on the predetermined reference indicator, whether an X-ray radiation device including the X-ray emission surface is arranged at a predetermined position.

7. The method of claim 6, further comprising displaying, based on a result of the determining, the predetermined position.

8. The method of claim 1, further comprising determining whether an X-ray radiation device including the X-ray emission surface is arranged at a predetermined position, based on whether the second detector shape corresponds to the shape of the reference detector.

9. The method of claim 1, further comprising:
   receiving, from a user, a control signal for controlling movement of the X-ray emission surface;
   moving the X-ray emission surface in response to the received control signal;
   generating a third image by performing a second correction on the first image, wherein the second correction comprises changing the first detector shape to match a third detector shape photographed in a direction perpendicular to the moved X-ray emission surface; and
   displaying the generated third image.

10. The method of claim 1, wherein the performing of the correction on the first image comprises distorting the first image such that the first detector shape matches the second detector shape.

11. An X-ray image capturing apparatus comprising:
    a camera configured to acquire a first image by photographing a detector configured to receive X-rays emitted from an X-ray emission surface;
    at least one processor configured to:
      generate a second image by image processing the first image, wherein the image processing comprises performing a correction on the first image, wherein the correction comprises changing a first detector shape in the first image to match a second detector shape photographed in a direction perpendicular to the X-ray emission surface, and
      identify that the second detector shape corresponds to a shape of a reference detector included in a reference image captured in a direction perpendicular to a surface of the detector opposite the X-ray emission surface; and
    a display configured to display the second image with the shape of the reference detector,
    wherein the at least one processor is further configured to correct the first image based on a position of the X-ray emission surface, and a position of the camera.

12. The X-ray image capturing apparatus of claim 11, wherein the at least one processor is further configured to correct the first image based on a position of a center of the X-ray emission surface, and a position of a center of a lens of the camera.

13. The X-ray image capturing apparatus of claim 11, wherein the at least one processor is further configured to correct the first image based on a distance between the X-ray emission surface and the detector.

14. The X-ray image capturing apparatus of claim 11, wherein the at least one processor is further configured to correct the first image based on a predetermined reference indicator for determining at least one of a position of the detector and the first detector shape.

15. The X-ray image capturing apparatus of claim 14, wherein the display is further configured to display the predetermined reference indicator together with the second image.

16. The X-ray image capturing apparatus of claim 14, wherein the at least one processor is further configured to determine, based on the predetermined reference indicator, whether an X-ray radiation device including the X-ray emission surface is arranged at a predetermined position.

17. The X-ray image capturing apparatus of claim 11, wherein the at least one processor is further configured to determine whether an X-ray radiation device including the X-ray emission surface is arranged at a predetermined position, based on whether the second detector shape corresponds to the shape of the reference detector.

18. The X-ray image capturing apparatus of claim 11, further comprising an input device configured to receive from a user a control signal for controlling movement of the X-ray emission surface,
   wherein the at least one processor is further configured to control the X-ray emission surface to move in response to the received control signal and generate a third image by performing a second correction on the first image, wherein the second correction comprises changing the first detector shape to match a third detector shape photographed in a direction perpendicular to the moved X-ray emission surface, and
   wherein the display is further configured to display the generated third image.

19. The X-ray image capturing apparatus of claim 11,
   wherein the detector is an electronic X-ray detector configured to convert the X-rays into electrical signals,
   wherein the X-ray emission surface is located in an emission plane parallel to the surface of the detector,
   wherein the camera is located in the emission plane, and is offset from the X-ray emission surface in a direction parallel to the emission plane, and
   wherein the first image is obtained by photographing the surface of the detector by the camera directly in a direction non-perpendicular to the emission plane.

* * * * *